US009003582B2

(12) United States Patent  (10) Patent No.: US 9,003,582 B2
Armbruster  (45) Date of Patent: Apr. 14, 2015

(54) SOUND PILLOW SLEEP SYSTEM

(71) Applicant: Armbruster Enterprises, Inc., San Antonio, TX (US)

(72) Inventor: Robert Scott Armbruster, San Antonio, TX (US)

(73) Assignee: Armbruster Enterprises, Inc., San Antonio, TX (US)

( * ) Notice: Subject to any disclaimer, the term of this patent is extended or adjusted under 35 U.S.C. 154(b) by 76 days.

(21) Appl. No.: 13/623,592

(22) Filed: Sep. 20, 2012

(65) Prior Publication Data

US 2013/0079584 A1  Mar. 28, 2013

Related U.S. Application Data

(60) Provisional application No. 61/538,430, filed on Sep. 23, 2011.

(51) Int. Cl.
*A47G 9/10* (2006.01)
*A61M 21/02* (2006.01)
*A61M 21/00* (2006.01)

(52) U.S. Cl.
CPC ............ *A61M 21/02* (2013.01); *A47G 9/1045* (2013.01); *A61M 2021/0027* (2013.01); *A61M 2205/3561* (2013.01); *A61M 2205/3592* (2013.01); *A61M 2205/8206* (2013.01); *Y10S 5/904* (2013.01)

(58) Field of Classification Search
CPC ...... A47G 9/10; A47G 9/1009; A47G 9/1045
USPC ................. 5/639, 904; 381/333, 388
See application file for complete search history.

(56) References Cited

U.S. PATENT DOCUMENTS

| 2,000,523 | A | * | 5/1935 | Knapp | 381/388 |
| 3,384,719 | A | * | 5/1968 | Lanzara | 381/301 |
| 4,038,499 | A | | 7/1977 | Yeaple | |
| 4,782,533 | A | | 11/1988 | Haynie | |
| 4,862,438 | A | | 8/1989 | Fry | |
| 5,123,133 | A | | 6/1992 | Albert | |
| 5,201,002 | A | | 4/1993 | Dahlem | |

(Continued)

FOREIGN PATENT DOCUMENTS

| AU | 22009/92 B | 10/1993 | | |
| GB | 2113502 A | * 8/1983 | ............... | H04R 1/02 |
| WO | WO 2013/043885 A1 | * 3/2013 | ............... | A47G 9/10 |

OTHER PUBLICATIONS

International Search Report and Written Opinion, International Application No. PCT/US2012/056360, dated Dec. 18, 2012, 9 pages.

*Primary Examiner* — Michael Trettel
(74) *Attorney, Agent, or Firm* — Hoffmann & Baron, LLP

(57) ABSTRACT

Provided is a pillow and method of marking the pillow to mitigate tinnitus. The pillow includes a first and second portions of fill material, an anchor strip assembly and a pillow casing. The anchor strip assembly is disposed between the first and second portions of fill material. The anchor strip assembly includes an anchor strip and a plurality of speakers secured to the anchor strip at a distance from each other. A first and second edge portions the anchor strip extends beyond edges of the first and second portions of fill material. The pillow casing secures the anchor strip assembly disposed between the first and second portions of the fill material inside the pillow casing such that the first and second edge portions of the anchor strip are secured respectively between a first and second seams of the pillow casing.

20 Claims, 5 Drawing Sheets

(56) References Cited

U.S. PATENT DOCUMENTS

| | | |
|---|---|---|
| 5,313,678 A | 5/1994 | Redewill |
| 5,974,607 A | 11/1999 | Smith |
| 6,044,161 A | 3/2000 | Lee |
| 6,704,958 B2 | 3/2004 | Gohl |
| 7,520,851 B2 | 4/2009 | Davis et al. |
| 7,627,917 B2 | 12/2009 | Vandenbelt |
| 7,685,661 B2 | 3/2010 | Popilek et al. |
| 8,056,167 B2 * | 11/2011 | Cheung et al. ............ 5/639 |
| 2007/0160244 A1 * | 7/2007 | Hedaya ............ 381/333 |
| 2009/0089931 A1 | 4/2009 | Vandenbelt |
| 2010/0097197 A1 | 4/2010 | Sowada |

* cited by examiner

SOUND PILLOW SLEEP SYSTEM

CROSS REFERENCE TO RELATED APPLICATION

This application claims priority to and benefit of U.S. Provisional Patent Application No. 61/538,430 filed on Sep. 23, 2011, the disclosure of which is incorporated in its entirety by reference herein.

BACKGROUND

1. Field

The present application relates to pillows. More specifically, the present application is directed to a sound pillow sleep system having a pillow with a speaker assembly and a method of manufacturing the pillow with the speaker assembly.

2. Brief Discussion of Related Art

Tinnitus is the perception of sound within the human ear in the absence of corresponding external sound. Tinnitus is a condition that can result from a wide range of underlying causes, such as, neurological, infectious, allergenic, foreign object or wax build-up in the ear, exposure to noise, as well as myriad other causes.

Hearing loss can be accompanied by tinnitus. While tinnitus can result from natural/congenital hearing loss, the most common cases of tinnitus are a result of loud noise, which often induces a level of hearing loss. Some researchers have found that frequencies tinnitus sufferers cannot hear as a result of their hearing loss are similar to subjective frequencies that the sufferers hear as a result of their tinnitus. These frequencies tend to be higher-end frequencies.

Invariably, rest and especially sleep are among a body's/mind's numerous mechanisms for natural healing from the physical and nervous assaults that the body/mind endured throughout the previous day. In many cases, tinnitus sufferers, as well as other individuals who experience sleep disorders for any number of reasons (e.g., post-traumatic stress disorder, addiction, insomnia, and/or other reason), cannot take advantage of such relaxation or healing sleep because their tinnitus or other sleep disorder(s) makes falling asleep or staying asleep extremely difficult. As a result these people suffer unrelentingly or are relegated to medications that can have significant adverse side effects.

Conventional pillows, which include a pillow casing and fill material, are known in the art and they have not undergone significant changes in the many years of pillow making. While there have been attempts to incorporate speaker assemblies into specialty pillows made of elastically-deformable (e.g., foam) materials that can secure the speaker assemblies, such integration into conventional pillows has met with difficulties. Specifically, it is difficult to integrate a speaker assembly into a conventional pillow because the fill material cannot secure the speaker assembly effectively, which increases the likelihood of the speaker assembly shifting from desired orientation during operation.

There exists a need in the art to provide a sound pillow sleep system having a pillow that secures a speaker assembly in a desired orientation in relation to the pillow casing and the fill material of the pillow to reduce the potential for shifting of the speaker assembly from the desired orientation and to improve the focusing of the speaker assembly output toward the head/ears of a tinnitus or sleep deprivation sufferer, while providing masking of tinnitus to facilitate comfortable, restful and therapeutic sleeping for a tinnitus sufferer and at the same time mitigating sleeping disruption to the sufferer's significant other who may be in proximity of the pillow.

SUMMARY

In accordance with an embodiment, a pillow is disclosed. The pillow includes a first and second portions of fill material, an anchor strip assembly and a pillow casing. The anchor strip assembly is disposed between the first and second portions of fill material. The anchor strip assembly includes an anchor strip and a plurality of speakers secured to the anchor strip at a distance from each other. A first and second edge portions of the anchor strip extend beyond edges of the first and second portions of fill material. The pillow casing secures the anchor strip assembly disposed between the first and second portions of fill material inside the pillow casing such that the first and second edge portions of the anchor strip are secured respectively between a first and second seams of the pillow casing.

In accordance with another embodiment, a method of manufacturing a pillow a pillow is disclosed. According to the method, a first and second portions of fill material are provided. An anchor strip assembly is disposed between the first and second portions of fill material. The anchor strip assembly includes an anchor strip and a plurality of speakers that are secured to the anchor strip at a distance from each other. A first and second edge portions of the anchor strip extend beyond edges of the first and second portions of fill material. The anchor strip assembly disposed between the first and second portions of fill material is secured inside the pillow casing such that the first and second edge portions of the anchor strip are secured respectively between a first and second seams of the pillow casing.

These and other purposes, goals and advantages of the present application will become apparent from the following detailed description of example embodiments read in connection with the accompanying drawings.

BRIEF DESCRIPTION OF THE DRAWINGS

Some embodiments are illustrated by way of example and not limitation in the figures of the accompanying drawings in which.

DETAILED DESCRIPTION

A sound pillow sleep system having a pillow with a speaker assembly and a method of manufacturing the pillow with the speaker assembly are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details.

Figure 1:
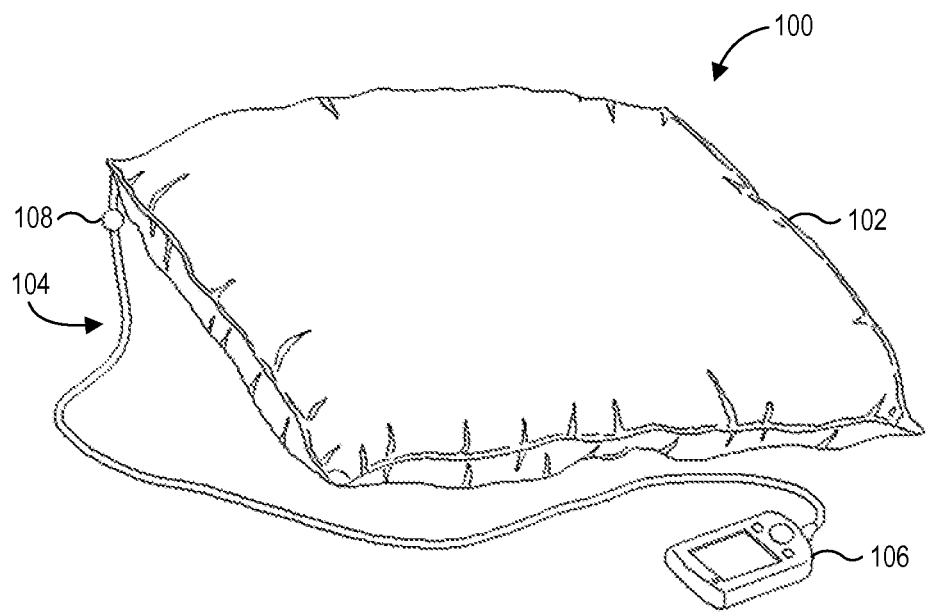
FIG. 1 illustrates a top perspective view of an example sound pillow sleep system.

FIG. 1 illustrates a top perspective view of an example sound pillow sleep system 100. In this example, the sound pillow sleep system 100 includes a pillow 102, a speaker assembly 104, and a signal source 106.

The pillow 102 includes a pillow casing and a fill material, as will be described in greater detail hereinafter. At this point it is sufficient to mention that the pillow casing can be made of cotton, a combination of cotton and another material (e.g., polyester-cotton combination), or any other conventional material or combination of materials (e.g., silk, satin and/or other materials). The fill material can be a slick fiberfill (e.g., silicon-coated material), a dry fiberfill (e.g., a garneted material), as well as any other fill material that can be inserted into a pillow casing to provide pillow 102. In various embodiments, the fiberfill can be made of polyester (e.g., spun fiber) to allow an output audio signal (e.g., sound) from the speaker assembly 104 to more easily penetrate through the fiberfill such that it can be heard by a user.

The speaker assembly 104 is secured or integrated inside the pillow 102 in a desired position and orientation in relation to the pillow 102 (pillow casing and fill material) such that the potential for shifting of the speaker assembly 104 can be reduced, as will be described hereinafter in greater detail. The speaker assembly 104 is configured to connect to the signal source 106, whether in a wireless or wired configuration, in order to receive an input audio signal (e.g., mono/stereo signal) that can be audibly communicated via a plurality of speakers (e.g., stereo speakers) of the speaker assembly 104 through the pillow 102 to a user (e.g., tinnitus sufferer or another individual with a sleeping disorder(s)).

In some embodiments, the speaker assembly 104 is configured to convert or adjust the input audio signal to a converted output audio signal that provides a masking effect for tinnitus sufferers in a natural and comfortable position, which facilitates therapeutic sleep for the user using the pillow 102, as will further be described hereinafter. For example, the speaker assembly 104 can provide an output audio signal that includes a desired acoustic frequency-based response in relation to the input audio signal, which can facilitate comfortable tinnitus masking and restful/therapeutic sleep for the tinnitus sufferer. In other embodiments, the speaker assembly 104 is configured to audibly output the input audio signal to an output audio signal without such acoustic frequency-based response conversion (e.g., unconverted output audio signal) to facilitate comfortable, restful and therapeutic sleeping for the user using the pillow 102. In various embodiments, the speaker assembly 104 can include a volume control device 108 to control the volume of the output audio signal.

The signal source 106 is configured to connect to the speaker assembly 104, whether in a wireless or wired configuration, to provide the input audio signal (e.g., nature sounds, speech, music, or other audio) to the speaker assembly 104, which then audibly communicates a converted (desired acoustic frequency-based) output audio signal or an unconverted output audio signal to the user.

The signal source 106 can be a device such as a radio, a compact disk (CD) player, a portable media player (e.g., iPod®), a mobile phone, a computer (e.g., laptop, desktop, or other computing device), or any other signal source that can provide the input audio signal, whether in a wired or wireless configuration. In wired configurations, the speaker assembly 104 can connect to the signal source 106 via a headphone jack (e.g., ⅛" headphone jack) or another wired interface. In the wired embodiments, the signal source 106 is disposed externally to the pillow 102.

In some wireless configurations, the speaker assembly 104 can connect to the signal source 106 via a wireless communication interface (e.g., Bluetooth) or another wireless communication interface to stream the input audio signal to the speaker assembly 104. In other wireless configurations, the speaker assembly 104 can include the signal source 106 (e.g., radio receiver, music storage device, or other signal source). Such a signal source can be disposed on a chip (e.g., system on a chip—SoC), which is integrated with the speaker assembly 104. In the wireless embodiments, the wireless communication interface or the signal source is integrated at least partially (or fully) inside the pillow 102. In these wireless embodiments, the pillow 102 does not have to be tethered to the signal source 106 during operation, which can improve the comfort, rest and therapeutic sleep of the user during the use of the pillow 102.

In some embodiments, the signal source 106 can be a specifically programmed/configurable digital player having a memory and a display (e.g., touch screen display). Such a digital player can store one or more configurable audio folders each of which can include one or more audio files that can be played in the memory. The digital player supports MP3, WAV and WMA audio files, among others.

The digital player includes audio play controls (e.g., play/pause, stop, fast forward, fast rewind), as well as configurable play control settings to tailor play cycles to the user's needs. The configurable play control setting settings can include single audio file repeat, repeat all audio files, play all audio files once, and/or one or more other configurable play control settings.

The digital player can also include various configurable control settings, such as, equalizer control settings to modify acoustic frequency-based output for various acoustic frequencies, display control settings to adjust the length of the display illumination, language control settings to change language used to interact with the digital player, and power mode control settings to invoke or adjust sleep mode of the digital player.

The foregoing configurable settings can be selected by one or more buttons, whether hard buttons on the digital player or soft buttons on the display, and the selected settings can be stored in a configurable setting file in the memory of the digital player. The digital player uses the selected settings stored in the configurable setting file to adjust the operation of the digital player to user's selected settings.

The equalizer control settings described above enable the user to tailor the frequency response of the output audio signal from the wired/wireless speaker assembly as described herein. Specifically, the digital player can include a programmable integrated circuit, which in response to user selection via equalizer control settings can further adjust the frequency response of the output audio signal for various frequencies.

In some embodiments, the digital player is programmed to start playing when the power mode of the digital player is switched to "on." The digital player enables switching between audio folders upon selection of a button, and starts playing an audio file in the audio folder. The digital player also enables the user to select an audio file to play. The digital player can be programmed to fade out while playing a current audio file when the user selects another audio file and to fade in when the selected audio file begins playing.

The signal source 106, such as the digital player, can include or play audio files specifically designed to induce sleep and to keep the user sleeping, which can increase the likelihood that the user will experience all sleep stages, critical for the daily maintenance and healing of the user's body and mind.

For example, the digital player can be loaded with any or one or more of the following audio files: binaural, nature sounds, white and/or pink noise, and affirmations.

The binaural music and binaural nature-sound audio files can be designed for use with the sound pillow sleep system 100. These audio files can be recorded to factor in the spacing between the ears or "head shadow" of the user (the natural spacing of the user's ears and the head positioning) to create a three-dimensional effect. In traditional audio systems and recording, the head shadow is not taken into account.

Figure 3:
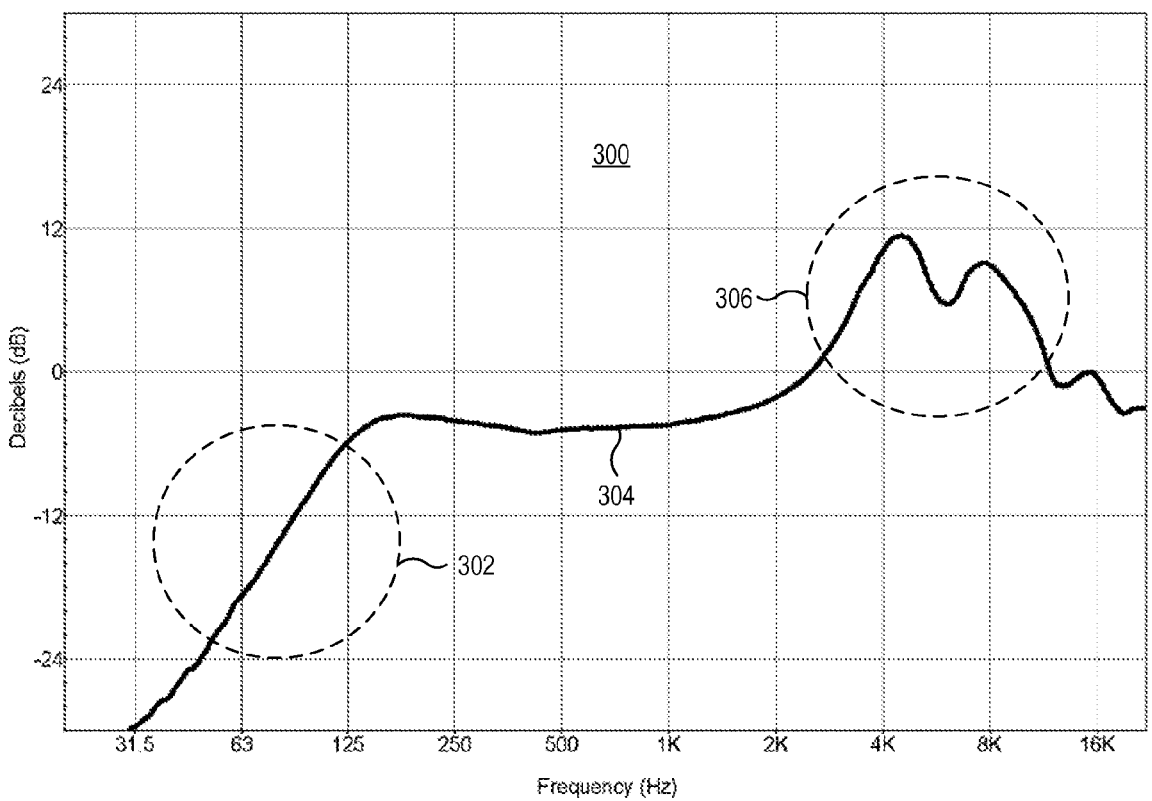
FIG. 3 illustrates a frequency transfer function to demonstrate an acoustic frequency response of example speakers in outputting an output audio signal in response to an input audio signal received from a signal source.

It is noted that in the speakers described herein, output in specific low-end acoustic frequency ranges was left in order to audibly communicate the binaural audio files as described hereinabove. The low-end acoustic frequency ranges, which include the binaural audio tones, are generally in the range of about 31.5 Hz to about 125 Hz, as illustrated in the example of FIG. 3.

The binaural audio files are designed to be hypnotic. Many of the chords are held for 10-15 seconds and evolve slowly from chord-to-chord so as not to disturb the user with sudden changes in tempo or volume. The evolving chords, slow tempos, and binaural tones are designed to induce a state of relaxation and ultimately sleep. The binaural audio files induce theta waves in the user's brain to slow brain activity, such that the brain entrains on the audio output and enters a deep/deeper state of relaxation and stays relaxed throughout the listening experience. Moreover, the binaural audio files also include binaural audio tones within the delta range that are designed to induce sleep.

Figure 2A:
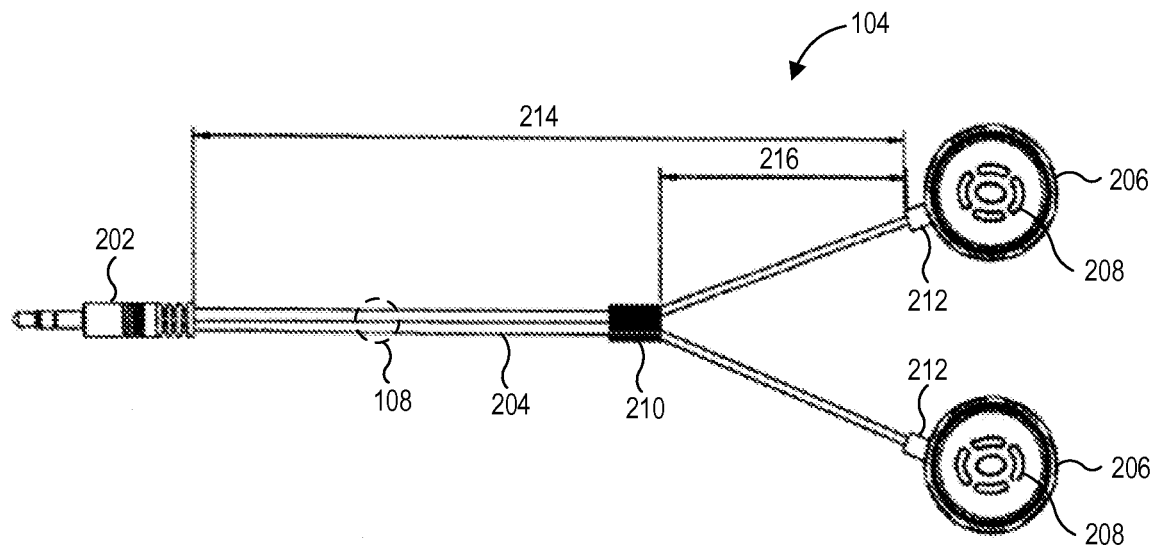
FIG. 2A illustrates an embodiment of an example wired speaker assembly.

FIG. 2A illustrates an embodiment of an example wired speaker assembly 104. The speaker assembly 104 includes a connector 202, a cord 204 and stereo speakers 206.

The connector 202 can be a headphone jack connector (e.g., standard ⅛" headphone jack connector), a universal serial bus (USB) connector, or any other connector configured to connect to a reciprocal jack or interface in the signal source 106 and further configured to transmit the output audio signal from the signal source 106 to the stereo speakers 206 via the cord 204.

The cord 204 connects the connector 202 to the stereo speakers 206. In some embodiments, the cord 204 includes a volume control device 108 to enable the user to control the volume of the output audio signal. The volume control device 108 can be disposed anywhere along the cord 204. In some embodiments, the cord 204 can have an overall length 214 from about 6.5 feet to about 7.5 feet. The overall length 214 of the cord 204 can be increased or decreased in various embodiments to accommodate a variety of applications of the sound pillow sleep system 100.

A reinforcement sleeve (or tube) 210 is provided over the cord 204, which reinforces a split in the cord 204 to the left speaker and the right speaker of the stereo speakers 206. The reinforcement tube 210 is adjustable in relation to the cord 204. A length 216 of the split cord 204 is about 11 inches. The length 216 can be increased or decreased in various embodiments to accommodate different separation between the stereo speakers 206, as will be described hereinbelow with reference to FIG. 6.

The left and the right portions after the split in the cord 204 can have the same or different lengths. The cord 204 is also reinforced at the entry point to each speaker 206 with a reinforcement member 212 in the side of the speaker housing. Such reinforcement members 212 secure the cord 204 to the speakers 206 to help mitigate the effects from wear-and-tear created during the user's many sleep position changes during use of the pillow 102.

Figure 4:
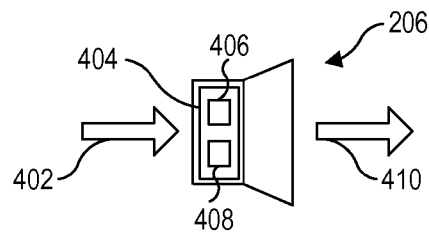
FIG. 4 is a schematic illustration of an example speaker in the wired speaker assembly or the wireless speaker assembly.

The housing of the stereo speakers 206 include openings 208 in the top of the housing to allow the output audio signal to be effectively propagated or transmitted from the stereo speakers 206, as also shown in FIG. 4 hereinbelow. The top and bottom of the housing of the speakers 206 are shown and described in greater detail with reference to FIGS. 5A and 5B hereinbelow.

Figure 2B:
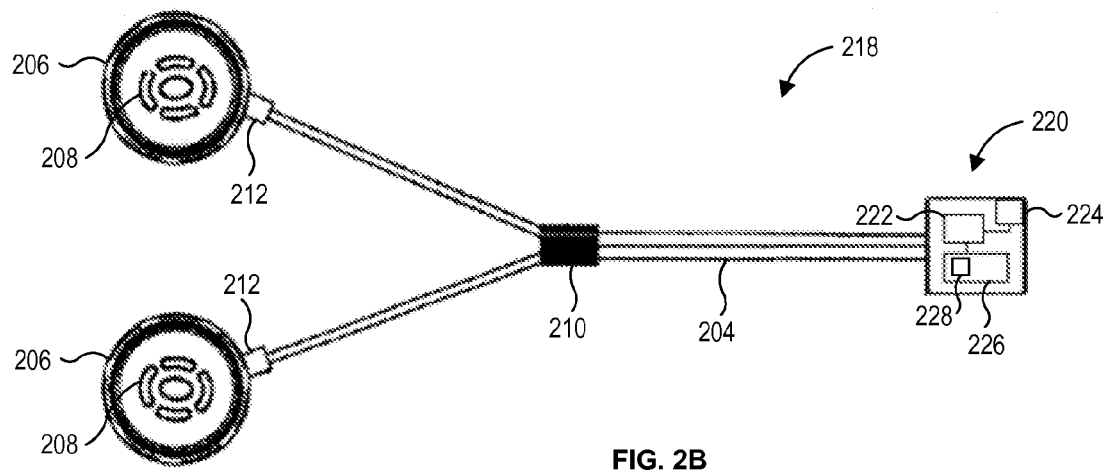
FIG. 2B illustrates an embodiment of an example wireless speaker assembly.

FIG. 2B illustrates an embodiment of an example wireless speaker assembly 218. The wireless speaker assembly 218 is generally similar to the speaker assembly 104, except for the wireless connector (or interface) 220. Similarly designated elements will not be described hereinafter. Thus, the speaker assembly 218 includes the wireless connector 220, the cord 204 and the stereo speakers 206.

The wireless connector 220 is configured to receive an input audio signal (e.g., mono/stereo signal) that can be audibly communicated via the stereo speakers 206 of the speaker assembly 218 through the pillow 102 to a user (e.g., tinnitus sufferer).

The wireless connector 220 includes a rechargeable battery 222, a power connector 224, and a wireless communication interface 226. The rechargeable battery 222 powers the speaker assembly 218 such that an input audio signal can be received by the wireless interface 226 and an output audio signal can be output by the stereo speakers 206. The rechargeable battery 222 can be charged through the power connector 224.

The power connector 224 can be a wired connector or a wireless connector. In the wired configuration, the power connector 224 includes a jack configured to receive a reciprocal power plug to charge the rechargeable battery 222. In the wireless configuration, the power connector 224 includes a first circuitry having an induction coil placed in proximity to a second external circuitry having an induction coil (not shown) in order to charge the rechargeable battery 222 using inductive charging.

In some wireless configurations, the wireless communication interface 226 is configured to receive an input audio signal from the signal source 106 (e.g., using Bluetooth or another wireless communication technology), optionally to amplify the received input audio signal, and then to provide the input audio signal to the stereo speakers 206. In other wireless configurations, the wireless communication interface 226 can include a signal source 228 (e.g., radio receiver, audio storage device, or another signal source), which can provide the input audio signal directed to the stereo speakers 206.

If the signal source 228 is a radio receiver, it can receive an input audio signal (e.g., AM, FM or another radio or television input audio signal) to be provided by the wireless communication interface 226 to the stereo speakers 206. In such cases, the wireless communication interface 226 can include a switch to turn the input audio signal on or off. One or more tuning controls can provide further functionality to select the radio/television frequency. If the signal source is an audio storage device it can store one or more digital input audio files (loaded by wired or wireless connection), which the wireless communication interface 226 can processes into the input audio signal and can provide the input audio signal to the stereo speakers 206. In such cases, the wireless communication interface 226 can include a switch to turn the input audio signal on or off. One or more audio play controls can provide further functionality associated with stored input audio files, such as play/pause, stop, fast forward, and fast rewind.

FIG. 3 illustrates a frequency transfer function 300 to demonstrate an acoustic frequency response of the speakers 206 in outputting the output audio signal in response to the input audio signal received from the signal source 106. As will be described hereinafter in greater detail, in generating the output audio signal, the input audio signal is attenuated for first acoustic frequencies, maintained approximately flat for second acoustic frequencies, and amplified for third acoustic frequencies.

In a lower-end first frequency range (e.g., about 30 Hz to about 200 Hz) 302, the acoustic output of the output audio signal has been reduced or attenuated from that of input audio signal. Specifically, the acoustic output from about 200 Hz to about 30 Hz has an approximate roll-off response curve attenuated from about −4 dB to about −30 dB. This frequency response curve allows optimization with increased efficiency in the higher-end third frequency range (e.g., intelligibility band), as described hereinbelow. More specifically, the reduction of acoustic output in the lower-end frequency range facilitates increased acoustic output in the high-end frequency range (e.g., intelligibility band).

In a middle second frequency range (e.g., about 200 Hz to about 2 KHz) 304, the acoustic output of the output audio signal is somewhat flat with respect to the input audio signal. Specifically, the acoustic output from about 200 Hz to about 2 KHz has an approximately flat response curve at about −4 dB to about −6 dB.

In a higher-end third frequency range (e.g., about 2 KHz to about 20 KHz) 306, the output audio signal has an amplified or increased acoustic output from that of input audio signal. Specifically, the acoustic output from about 3 KHz to about 10 KHz has a dramatically increased efficiency with an average acoustic output of about 11-12 dB above that of the second frequency range 304. For example, an average individual will perceive an increase of 10 dB in acoustic output as a doubling of loudness.

After reviewing audiograms, speaking with professionals in the audiology field and researching literature concerning tinnitus, it has been determined that the foregoing increase in acoustic output in the third frequency range 306 provides a desired compensation in those frequencies where some level of hearing sensitivity has been affected in tinnitus sufferers. Specifically, the increased acoustic output in the higher-end frequencies has been found to be effective in masking tinnitus.

In view of the foregoing, the stereo speakers 206 are configured to produce an attenuated acoustic output in the lower-end frequencies, an approximately flat acoustic output in the middle frequencies, and an increased acoustic output in the higher-end frequencies. Specifically, with reference to the intelligibility band—frequencies of the human voice and other natural sounds, e.g., from about 4 KHz to about 8 KHz—the acoustic output is amplified in order to make the output audio signal sound more natural and pleasing to the user, e.g., a tinnitus sufferer. This acoustic output in the intelligibility band, as well as the acoustic output in other higher-end frequencies, further aids those with some hearing impairment—whether from tinnitus or another factor(s)—to hear the output audio signal better due to the perceived and realized doubling of the acoustic output in the higher-end frequencies. Accordingly, the acoustic output in the third frequency range can effectively mask (or cover-up) the tinnitus of a tinnitus sufferer, especially tinnitus sufferers who have some hearing loss in the higher-end frequencies.

FIG. 4 is a schematic illustration of the example speaker 206 in the wired speaker assembly 104 or the wireless speaker assembly 218.

The speaker 206 includes electronics 404, which among other components includes a configurable attenuator 406 and an amplifier 408, configured to receive and convert an input audio signal 402 (e.g., from signal source 106) to an output audio signal 410 as described herein.

For example, the electronics 404 can include a programmable integrated circuit, such as an application specific integrated circuit (ASIC), which together with the attenuator 406 and amplifier 408 can generate output audio signal 410 from an input audio signal 402 in accordance with the transfer function, as illustrated in and described with reference to FIG. 3.

Figure 5A:
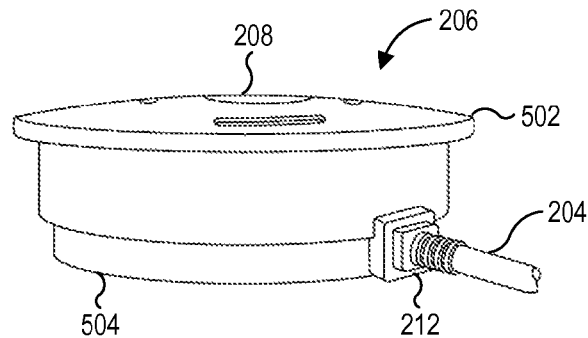
FIG. 5A is side view of an example speaker's housing in the wired speaker assembly or the wireless speaker assembly.

FIG. 5A is side view of an example speaker's 206 housing in the wired speaker assembly 104 or the wireless speaker assembly 218. The speaker 206 is configured to convert or adjust an input audio signal to a converted output audio signal, which among other things, masks tinnitus as described herein.

The housing of the speaker 206 has a diameter of approximately 1⅞" and a height of approximately ½". In various embodiments, a differently dimensioned speaker can be used. The housing generally has beveled edges and includes a convex top surface 502 and a generally planar bottom surface 504. The convex top surface 504 includes a plurality of openings 208 to allow an output audio signal generated by the speaker 206 to be communicated from the speaker 206 and through the pillow 102.

Beveled edges and the convex top surface 502 of the housing facilitate smooth integration into the pillow 102 such as to mitigate user's perception or feel of the speaker 206 in the pillow 102. The generally planar bottom surface 504 facilitates integration of the speaker 206 in the pillow 102, as will be described hereinbelow with reference to FIGS. 6A, 6B. As shown, the cord 204 can be reinforced by the reinforcement member 212 in the side of the housing.

The housing of the stereo speakers 206 includes audio openings 208 through the convex top surface 502 of the housing to allow the output audio signal to be effectively propagated or transmitted from the stereo speakers 206 through the pillow 102, such that the user—especially a user with some hearing impairment due to tinnitus or other factor(s)—can perceive the output audio signal during use of the sound pillow sleep system 100.

Figure 5B:
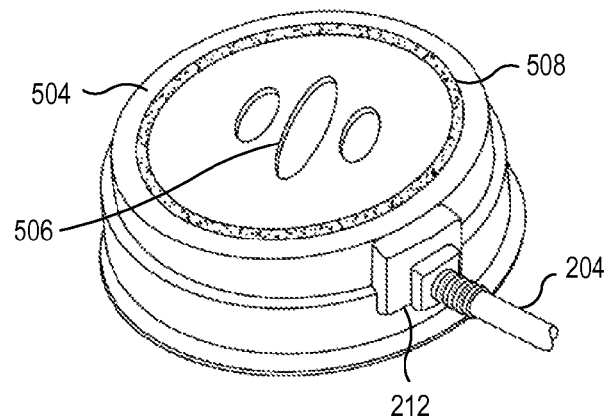
FIG. 5B is a back perspective view of the example speaker's housing in the wired speaker assembly or the wireless speaker assembly illustrated in FIG. 5A.

FIG. 5B is a back perspective view of the example speaker's 206 housing in the wired speaker assembly 104 or the wireless speaker assembly 218 illustrated in FIG. 5A.

The housing of the stereo speakers 206 additionally includes audio openings 506 through the planar bottom surface 504 of the housing to allow the output audio signal to be effectively propagated or transmitted from the stereo speakers 206 through the pillow 102, such that the user can perceive the output audio signal during use of the sound pillow sleep system 100. The audio openings 506 through the bottom surface 504 allow air to enter the back of the speakers 206 to provide a diaphragm (not shown) with the necessary air flow to generate the output audio signal. These audio openings 506 improve the generation and propagation of the output audio signal in the enclosed environment in which the speakers 206 are located (e.g., inside a pillow 102).

As shown, a bead of glue 508 is provided around at least a portion of the planar bottom surface 504 to facilitate integration of the speaker 206 into the pillow 102, as will be shown and described in detail with reference to FIGS. 6A, 6B hereinbelow.

Figure 6A:
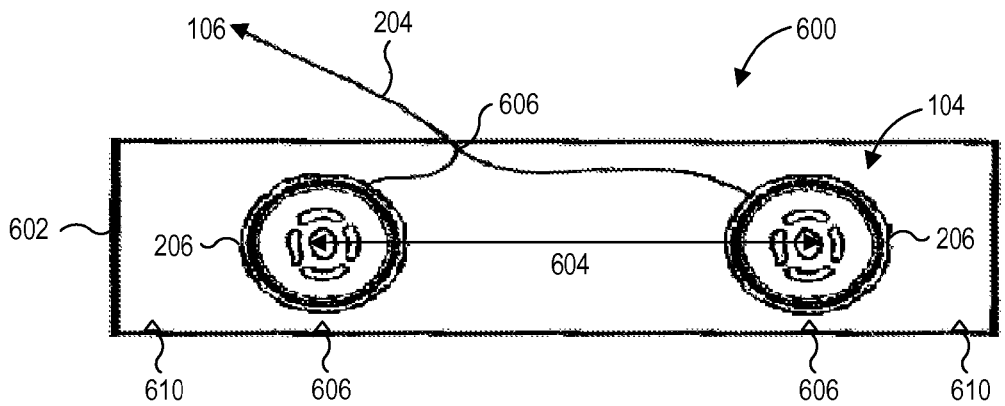
FIG. 6A illustrates an example anchor strip assembly securing the wired speaker assembly.

FIG. 6A illustrates an example anchor strip assembly 600 configured to secure the wired speaker assembly 104 in the pillow 102. The anchor strip assembly 600 includes an anchor strip 602 and the wired speaker assembly 104.

The anchor strip 602 is a strip or band of material—approximately 3"-5" width by 22" length—to which the speakers 206 of the speaker assembly 104 are secured. The length of the anchor strip 602 is longer than the length of the pillow casing such that the anchor strip 602 can be secured to the pillow 102, as will be described herein. The length and width dimensions of the anchor strip 602 can be adjusted based on speaker diameter, the length of the pillow 102, and user's ear position (e.g., based on neck length). The anchor strip 602 can be made of any material, such as for example, cotton, polyester, a different material, or different combinations of materials (e.g., poly-cotton blend).

The speakers 206 are secured at a distance 604 from one another to the anchor strip 602. The distance 604 can be selected to be based on approximate distance between a user's ears (e.g., average distance between human ears) to facilitate transmission of the output audio signal from the speakers 206 to the user's ears. The distance 604 is determined from a center of the diameters of the speakers 206. In some embodiments, such as for a full-sized pillow 102, the distance 604 can be from about 10" to about 14". In other embodiments, such as for a travel-sized pillow 102, the distance can be about 6" to about 10". The distance 604 can further be adjusted or modified to accommodate various head sizes of the user (e.g., distance between user's ears).

In some embodiments, the cord 204 of the wired speaker assembly 104 can further be secured at 606 (e.g., glued) to the anchor strip 602 to reinforce the construction of the anchor strip assembly 600. Thereafter, the cord 204 extends to the signal source 106.

In various embodiments, positioning markers can be marked on or cut in the anchor strip 602 to indicate, for example, the left and right seam engagement markers 610 with the pillow casing of the pillow 102, as well as left and right speaker engagement markers 606 for stereo speakers 206. The seam engagement markers 610 enable the anchor strip assembly 600 to be disposed approximately centrally in the pillow 102, while speaker engagement markers 606 enable the speakers to be disposed equidistantly in relation to the center of the anchor strip 602.

Figure 6B:
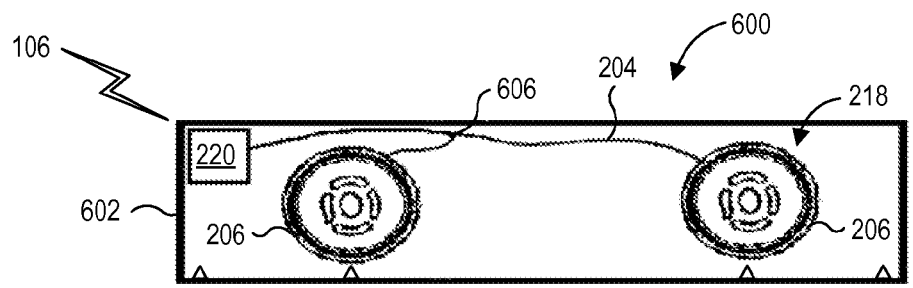
FIG. 6B illustrates the example anchor strip assembly securing the wireless speaker assembly.

FIG. 6B illustrates another example anchor strip assembly 600 configured to secure the wireless speaker assembly 218 in the pillow 102. In this embodiment, the anchor strip assembly 600 includes the anchor strip 602 and the wireless speaker assembly 218.

In the wireless embodiment, the wireless connector 220 of FIG. 2B is further secured at an edge of the anchor strip 602 (e.g., using glue) such that the wireless connector 220 can be disposed at a seam of the pillow 102, as will be described in greater detail hereinbelow. More specially, a bottom surface of the wireless connector 220, which can be generally planar, can receive a bead of glue that can secure the wireless connector 220 to the anchor strip 602. It is noted that while the wireless connector 220 is illustrated at the corner of the anchor strip 602, the wireless connector 220 can be secured anywhere along the width of the anchor strip 602.

The dimensions of the anchor strip 602 and the positioning of the speakers 206 can be the same or different than the wired embodiment described in FIG. 6A. The cord 204 in the wireless speaker assembly 218 can also be secured at 606 (e.g., glued) to the anchor strip 602 and is further secured to the wireless connector 220.

As already described herein, in some embodiments, the wireless connector 220 can wirelessly receive (e.g., via Bluetooth) an input audio signal from signal source 106, while in other embodiments, the wireless connector 220 can also include a signal source 228 (e.g., radio receiver, audio storage device, etc.) that can provide the input audio signal.

Figure 7A:
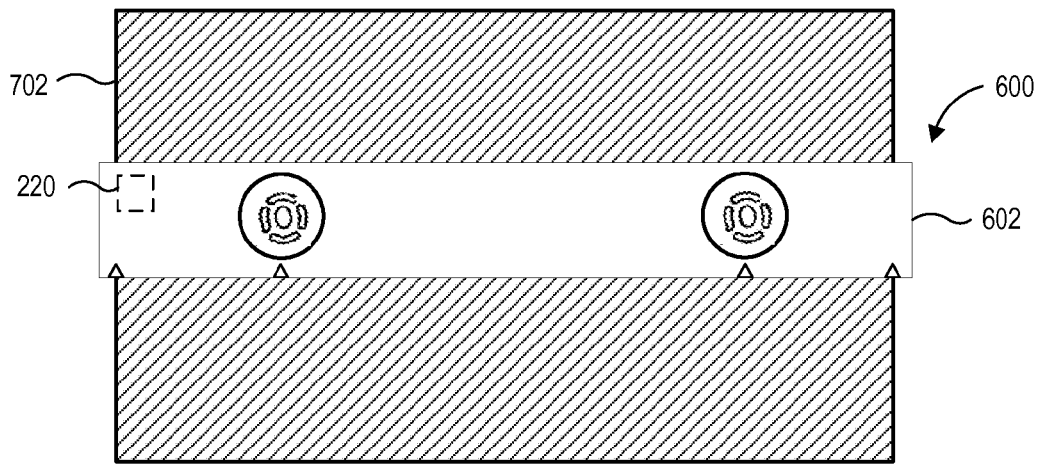
FIGS. 7A and 7B illustrate interior construction of the pillow.
Figure 7B:
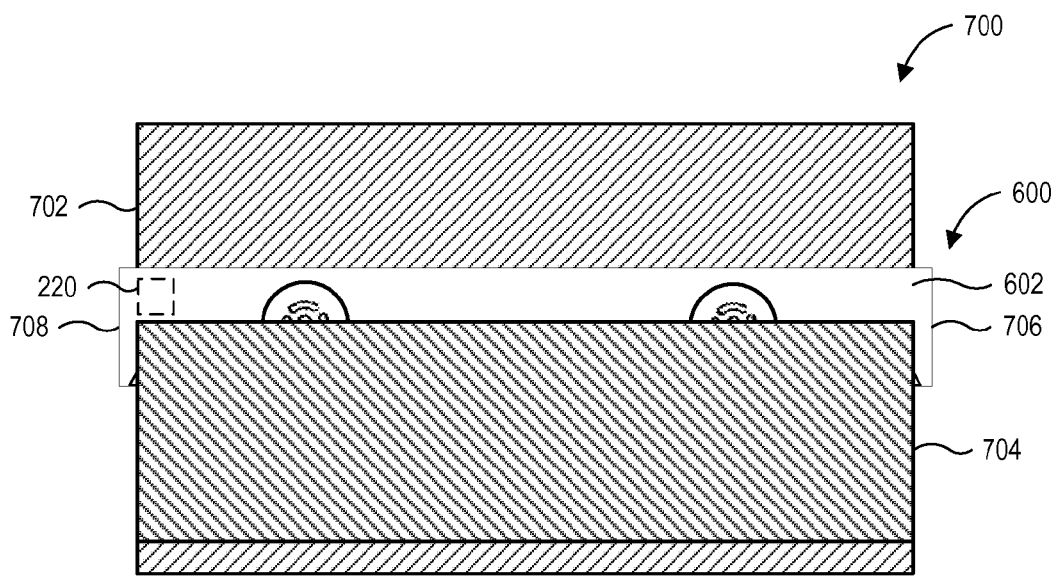

FIGS. 7A and 7B illustrate the interior construction of the pillow 102. As already described hereinabove, the pillow 102 includes a pillow casing described in FIGS. 8 and 9 and fill material 700 described immediately below with reference to FIGS. 7A and 7B.

As particularly shown in FIG. 7A, a first (bottom) portion 702 of fill material 700 is provided. The first portion 702 can be fiberfill made of 100% polyester (e.g., spun fiber). Moreover, the fiberfill can be dry (e.g., a garneted material) or slick (e.g., silicon-coated material), which and can be made into a sheet and folded into layers to form the first portion 702 of the fill material 700. Alternatively, the fiberfill of the first portion 702 can be amorphous (e.g., no layering). The first portion 702 has a length and width that can snugly fit into the pillow casing of the pillow 102. The height of the first portion 702 and a second portion 704, as shown in FIG. 7B, should fit snugly into the pillow casing of the pillow 102.

The anchor strip assembly 600 is disposed approximately centrally over the first portion 702 of the fill material 700. Specifically, the seam positioning markers 610 can be used to position the anchor strip assembly 600 appropriately in relation to edges of the first portion 702. In various embodiments, the anchor strip assembly 600 can be moved vertically (up or down) in relation to the first portion 702.

In wireless embodiments, the wireless connector 220 is disposed on the anchor strip 602 aligned with a seam positioning marker 610, such that it can be easier to charge the rechargeable batteries 222 via the power connector 224.

As particularly shown in FIG. 7B, the second (top) portion 704 of fill material 700 is disposed over the anchor strip assembly 600 (e.g., including the first portion 702 and the wired/wireless speaker assembly 104, 218), such respective edge portions 706, 708 extend beyond the fill material 700. The second portion 704 has approximately the same dimensions as the first portion 702, while being shown in cut-away fashion in FIG. 7B for clarity of the construction.

The second portion 704 can be made of the same material (fiberfill) or different material than the first portion 702, which can be made into a sheet folded into layers to form the second portion 704 of the fill material 700. Alternatively, the fiberfill of the second portion 704 can be amorphous (e.g., no layering). In some embodiments, a second portion 704 can be higher (more fiberfill) than the first portion 702 (less fiberfill), providing greater padding over the wired/wireless speaker assembly 104, 218. The fill material 700 (e.g., first portion 702 and second portion 704) with the anchor strip assembly 600 fit snugly into the pillow casing of the pillow 102.

Figure 8:
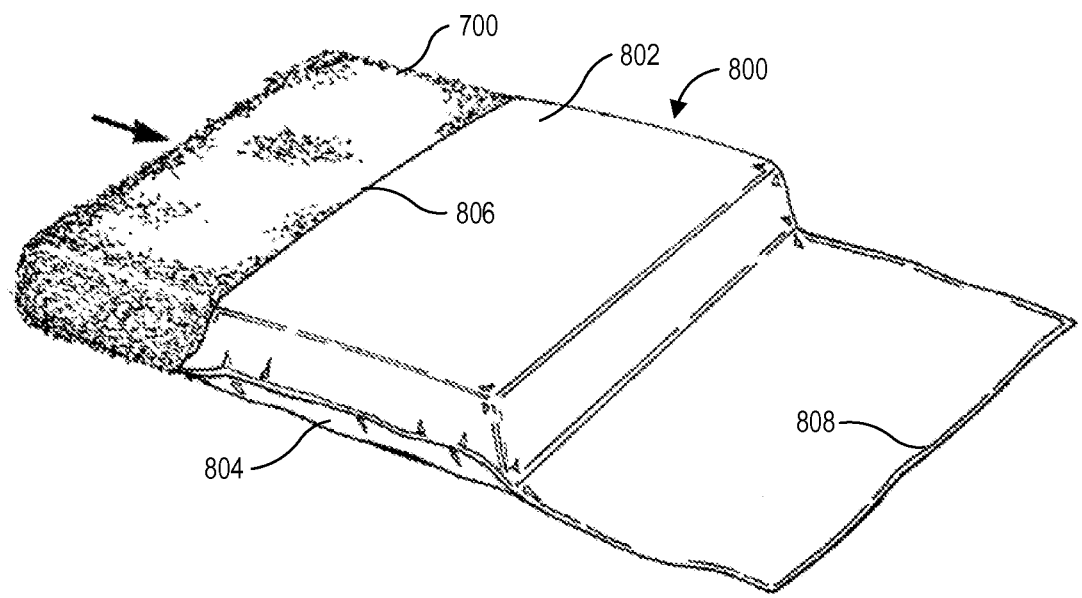
FIG. 8 illustrates insertion of the example anchor strip assembly integrated within the fill material into a pillow casing.

FIG. 8 illustrates insertion of the example anchor strip assembly 600 integrated within the fill material 700 into a pillow casing 800.

The pillow casing 800 of the sleeping pillow 102 can be made of two sheets of fabric (e.g., cotton-polyester) including a top sheet 802 and a bottom sheet 804. The sheets are sewn (stitched) together along two of the four edges thereof and the sheets are then inverted to provide the pillow casing 102, hiding the sewn seams to the interior of the pillow casing 102. The inverted pillow casing 800 includes open seams 806, 808 along the sides of the pillow casing 800.

The pillow casing 800 then receives or is filled with the fill material 700, which is integrated with the wired/wireless speaker assembly 104, 218, as particularly described with reference to FIGS. 7A, 7B. Seam engagement markers 610 in or on the anchor strip assembly 600, as best shown in FIG. 6A, can be used to line up the anchor strip assembly 600 with the open seams 806, 808. The open seams 806, 808 are then sewn to connect the sheets 802, 804, and the anchor strip 602 between the sheets 802,804 along the respective seams 806, 808.

In wired embodiments of the anchor strip assembly 600, the cord 204 extends through an opening (e.g., approximately at a corner of the pillow casing 800) between the sheets 802, 804 that is not sewn. In this case, the cord 204 can be glued in the opening to close such opening and to secure the cord 204 to the pillow casing 800.

In some wireless embodiments of the anchor strip assembly 600, the wireless connector 220 can extend partially through or be flush with an opening (e.g., approximately at a center along the width of the pillow casing 800) between the sheets 802, 804 that is not sewn. In this case, the wireless connector 220 can be glued in the opening to close such opening and to secure the wireless connector 220 to the pillow casing 800. In other wireless embodiments of the anchor strip assembly 600, wireless connector 220 can be completely sealed within the pillow casing 800.

Figure 9:
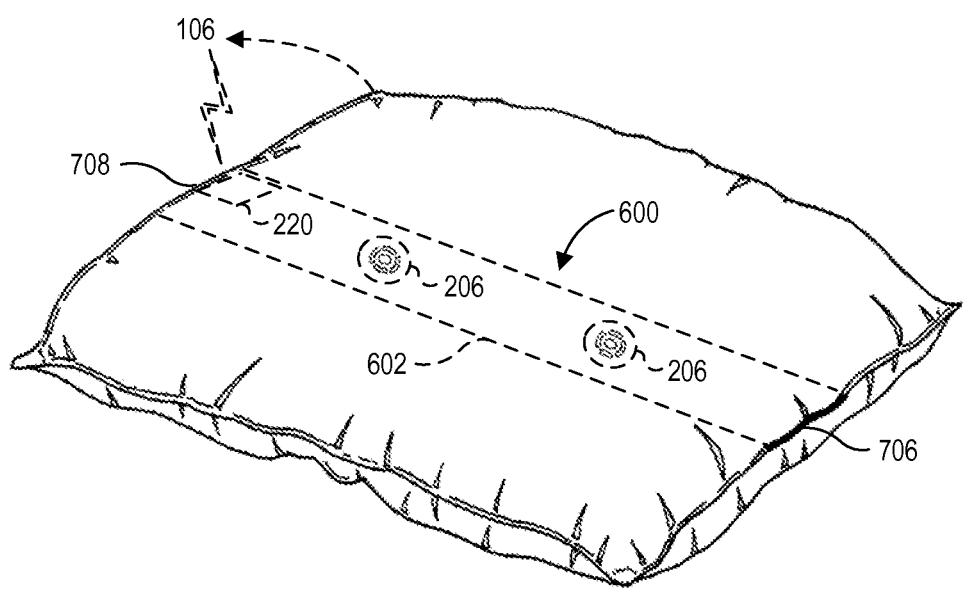
FIG. 9 illustrates the example pillow in which the anchor strip assembly and the fill material are integrated into the pillow casing.

FIG. 9 illustrates the example pillow 102 in which the anchor strip assembly 600 and the fill material 700 are integrated into the pillow casing 800.

The open seams 806, 808 are sewn and sealed as described hereinabove, such that the respective edge portions 706, 708 are sewn between the seams 806, 808, securing the anchor strip assembly 600 with respect to the fill material 700 and the pillow casing 800. Any openings used to integrate the cord 204 or the wireless connector 220 are sealed, such as by using glue. Thereafter, the respective edge portions 706, 708 are trimmed inline with the seams 806, 808 to complete the pillow 102.

The pillow 102 has dimensions including a length, width and height, such as 21"×15"×7" (e.g., full-sized pillow), 13"× 9"×5" (e.g., travel size pillow), or any other dimensioned pillow. Specifically, the pillow 102 can be of any conventional dimensions or otherwise any desirable dimensions into which anchor strip assembly 600 can be integrated, as described herein with reference to FIGS. 1-9.

In operation of the sound pillow sleep system 100 in accordance with FIGS. 1-9, the speakers 206 are secured to the anchor strip 602 and positioned comfortably beneath the head of the user near the user's ears to create an intimate listening experience via the wired/wireless signal source 106. Specifically, this positioning mitigates the output audio signal from disrupting the user's significant other or roommate who can be located in proximity to the pillow 102.

Moreover, the anchor strip 602 aids in focusing the output audio signal from speakers 206 towards the user's ears to enhance the listening experience and to reduce disruption to others. More specifically, when the user lies on the pillow 102, the weight of the user's head creates downward pressure on the anchor strip 602 that is met with resistance from the seams 806, 808 of the pillow casing 800, which causes the speakers 206 to angle toward the user's head and focuses the output audio signal towards the user's ears.

Thus, a sound pillow sleep system having a pillow with a speaker assembly and a method of manufacturing the pillow with the speaker assembly have been described. Although specific example embodiments have been described, it will be evident that various modifications and changes may be made to these embodiments without departing from the broader spirit and scope of the invention.

Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments shown are described in sufficient detail to enable those skilled in the art to practice the teachings disclosed herein. Other embodiments may be utilized and derived therefrom, such that structural and logical substitutions and changes may be made without departing from the scope of this application.

The foregoing detailed description, therefore, is not to be taken in a limiting sense, and the scope of various embodiments is defined only by the appended claims, along with the full range of equivalents to which such claims are entitled.

Although specific embodiments have been shown and described herein, it should be appreciated that any arrangement calculated to achieve the same purpose may be substituted for the specific embodiments shown. This application is intended to cover any and all adaptations or variations of various embodiments. Combinations of the above embodiments and other embodiments not specifically described herein, will be apparent to those of skill in the art upon reviewing the above description.

The Abstract is provided to comply with 37 C.F.R. §1.72(b) and will allow the reader to quickly ascertain the nature of the technical disclosure of this application. It is submitted with the understanding that it will not be used to interpret or limit the scope or meaning of the claims.

In the foregoing detailed description, various features may be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

Moreover, it is contemplated that the features or components of various embodiments described herein can be combined into different combinations that are not explicitly enumerated in the foregoing detailed description and that such combinations can similarly stand on their own as separate example embodiments that can be claimed.

The invention claimed is:

1. A pillow comprising:
    a first portion and a second portion of fill material;
    an anchor strip assembly disposed between the first portion and the second portion of fill material, the anchor strip assembly including an anchor strip and a plurality of speakers secured onto the anchor strip at a distance from each other such that the second portion of fill material is disposed at least atop the plurality of speakers, a first and second edge portions of the anchor strip extending beyond edges of the first portion and the second portion of fill material; and
    a pillow casing securing the anchor strip assembly disposed between the first portion and the second portion of fill material inside the pillow casing such that the first and second edge portions of the anchor strip are secured respectively between a first and second seams of the pillow casing.

2. The pillow of claim 1, wherein the plurality of speakers receives an input audio signal from a signal source and generates an output audio signal having a frequency-based acoustical response in relation to the input audio signal.

3. The pillow of claim 2, wherein the frequency-based acoustical response of the output audio signal is attenuated in relation to the input audio signal in a first frequency range.

4. The pillow of claim 3, wherein the first frequency range is from about 30 Hz to about 200 Hz.

5. The pillow of claim 2, wherein the frequency-based acoustical response of the output audio signal is approximately proportional in relation to the input audio signal in a second frequency range.

6. The pillow of claim 5, wherein the second frequency range is from about 200 Hz to about 2 KHz.

7. The pillow of claim 2, wherein the frequency-based acoustical response of the output audio signal is increased in relation to the input audio signal in a third frequency range.

8. The pillow of claim 7, wherein the third frequency range is from about 2 KHz to about 10 KHz.

9. The pillow of claim 2, wherein the frequency-based acoustical response of the output audio signal in relation to the input audio signal includes:
   a first frequency range where a first acoustical output roll-offs from about −4 dB to about −30 dB;
   a second frequency range where a second acoustical output is approximately proportional between about −4 dB and about −6 dB; and
   a third frequency range where a third acoustical output is increased to between about −4 dB and 11 dB.

10. The pillow of claim 9, wherein the third acoustical output is on average about 11 dB to about 12 dB greater than the second acoustical output.

11. The pillow of claim 2, wherein the plurality of speakers is connected by a cord to a signal source disposed outside the pillow casing.

12. The pillow of claim 2, wherein the anchor strip assembly further secures a wireless receiver to receive the input audio signal from a signal source disposed outside the pillow casing.

13. The pillow of claim 1, wherein the anchor strip is a sheet of material having a top surface and a bottom surface, and the plurality of speakers is secured to the top surface of the sheet.

14. The pillow of claim 13, wherein the plurality of speakers is glued or adhered to the top surface of the sheet.

15. The pillow of claim 2, wherein at least one speaker of the plurality of speakers includes a bottom surface and a top surface, the bottom surface including first audio openings to provide air flow into the at least one speaker in order to facilitate generation and communication of the output signal, the top surface including second audio openings to communicate the output audio signal as generated through the pillow.

16. A method for making a pillow, the method comprising:
   providing a first portion and a second portion of fill material; disposing an anchor strip assembly disposed between the first portion and the second portion of fill material, the anchor strip assembly including an anchor strip and a plurality of speakers secured onto the anchor strip at a distance from each other such that the second portion of fill material is disposed at least atop the plurality of speakers, a first and second edge portions of the anchor strip extending beyond edges of the first portion and the second portion of fill material;
   securing the anchor strip assembly disposed between the first portion and the second portion of fill material inside the pillow casing such that the first and second edge portions of the anchor strip are secured respectively between a first and second seams of the pillow casing.

17. The method of claim 16, further comprising:
   extending a cord from the plurality of speakers through an opening in a seam of the pillow casing to be connected to a signal source disposed outside the pillow casing; and
   sealing the cord in the opening of the pillow casing.

18. The method of claim 16, further comprising:
   securing a wireless receiver to the anchor strip assembly to receive an input audio signal from a signal source disposed outside the pillow, a first portion of the wireless receiver disposed in an opening of the pillow casing;
   connecting the plurality of speakers to the wireless receiver; and
   sealing the first portion of the wireless receiver in the opening of the pillow casing.

19. The method of claim 16, wherein the anchor strip is a sheet of material having a top surface and a bottom surface, and the plurality of speakers is secured to the top surface of the sheet.

20. The method of claim 19, wherein the plurality of speakers is glued or adhered to the top surface of the sheet.

* * * * *